United States Patent [19]

Trombley, III

[11] Patent Number: 5,254,101
[45] Date of Patent: Oct. 19, 1993

[54] FLUID PRESENCE INDICATOR FOR ROTATABLE SYRINGE

[75] Inventor: Frederick W. Trombley, III, Queensburry, N.Y.

[73] Assignee: Medrad, Inc., Indianola, Pa.

[21] Appl. No.: 983,078

[22] Filed: Nov. 27, 1992

[51] Int. Cl.$^5$ ............................................... A61M 5/18
[52] U.S. Cl. .................... 604/207; 604/187; 604/232
[58] Field of Search .............. 604/272, 264, 207, 232, 604/260, 181, 187; 73/327

[56] References Cited

U.S. PATENT DOCUMENTS

| | | | |
|---|---|---|---|
| 3,470,867 | 10/1969 | Goldsmith | 604/207 |
| 3,941,129 | 3/1976 | Pleznac | 604/207 |
| 4,018,223 | 4/1977 | Ethington | 604/207 |
| 4,178,071 | 12/1979 | Asbell | 604/207 |
| 4,594,073 | 6/1986 | Stine | 604/232 |
| 4,743,234 | 5/1988 | Leopoldi et al. | 604/207 |

Primary Examiner—John G. Weiss
Attorney, Agent, or Firm—Keck, Mahin & Cate

[57] ABSTRACT

A means for detecting the presence of a transparent liquid in the barrel of a transparent angiography syringe comprising a plurality of indicator patterns positioned on the exterior of the barrel, the indicator patterns arranged in a helical array circumscribing the barrel of the syringe. When the syringe is empty, each indicator pattern is seen as having a first elliptical configuration; however, when the fluid is present in the barrel, the indicator pattern appears to have a second circular configuration, and the difference in apparent configuration is indicative of the presence of the liquid. The indicator patterns are arranged in a non-overlapping array, to permit non-obstructed viewing of the patterns, as well as ready comparison of distorted and non-distorted patterns.

9 Claims, 2 Drawing Sheets

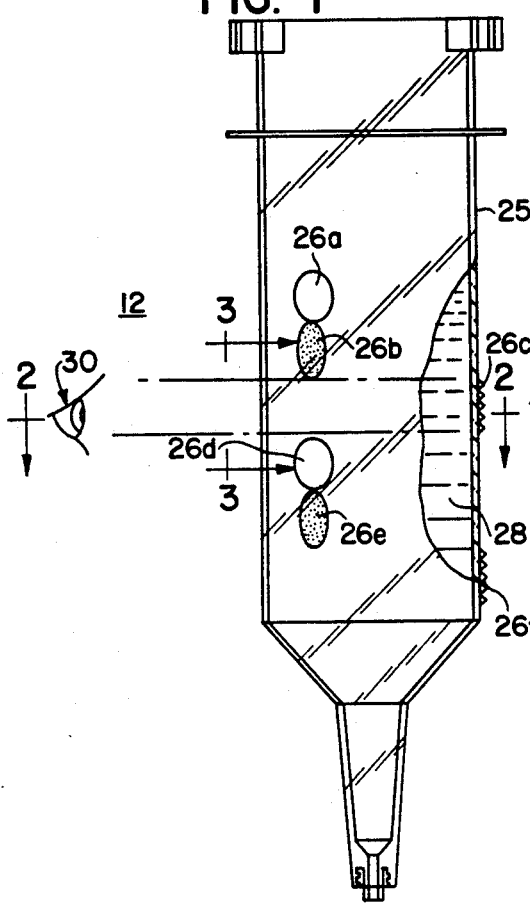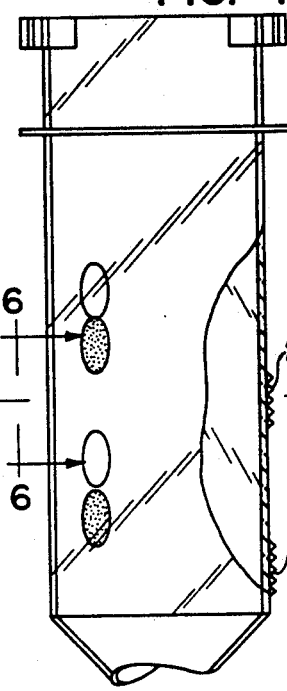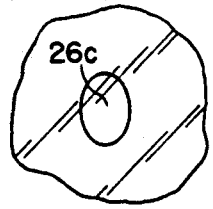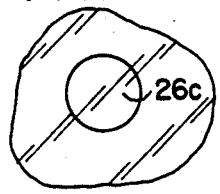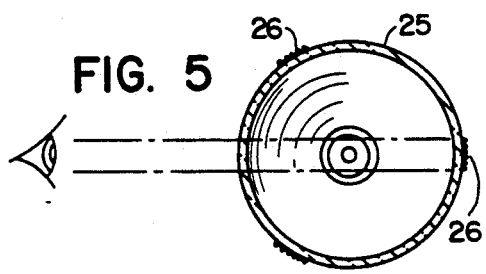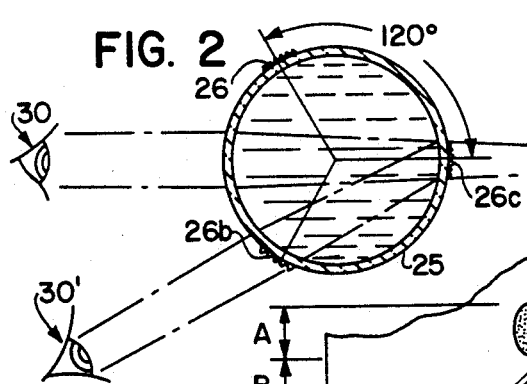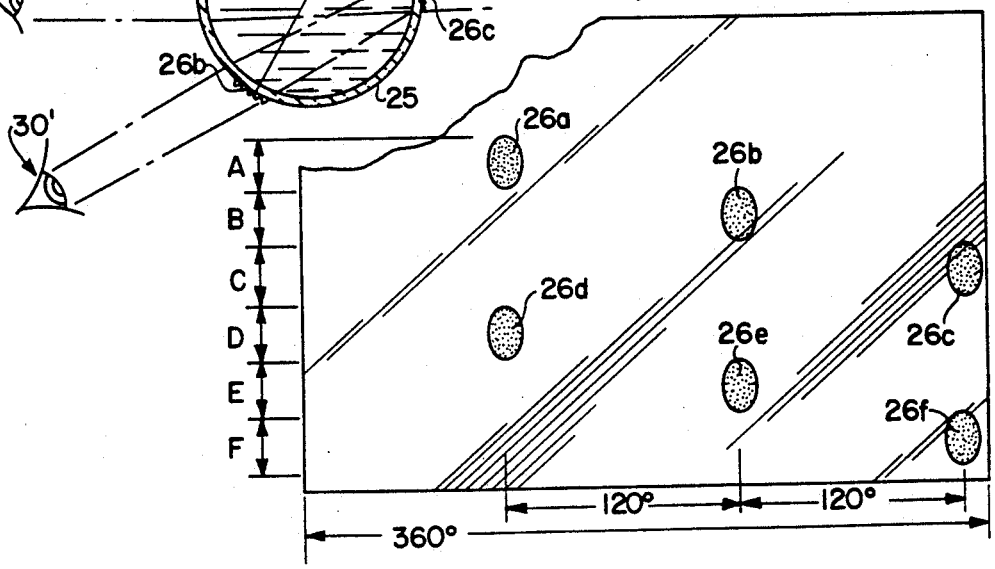

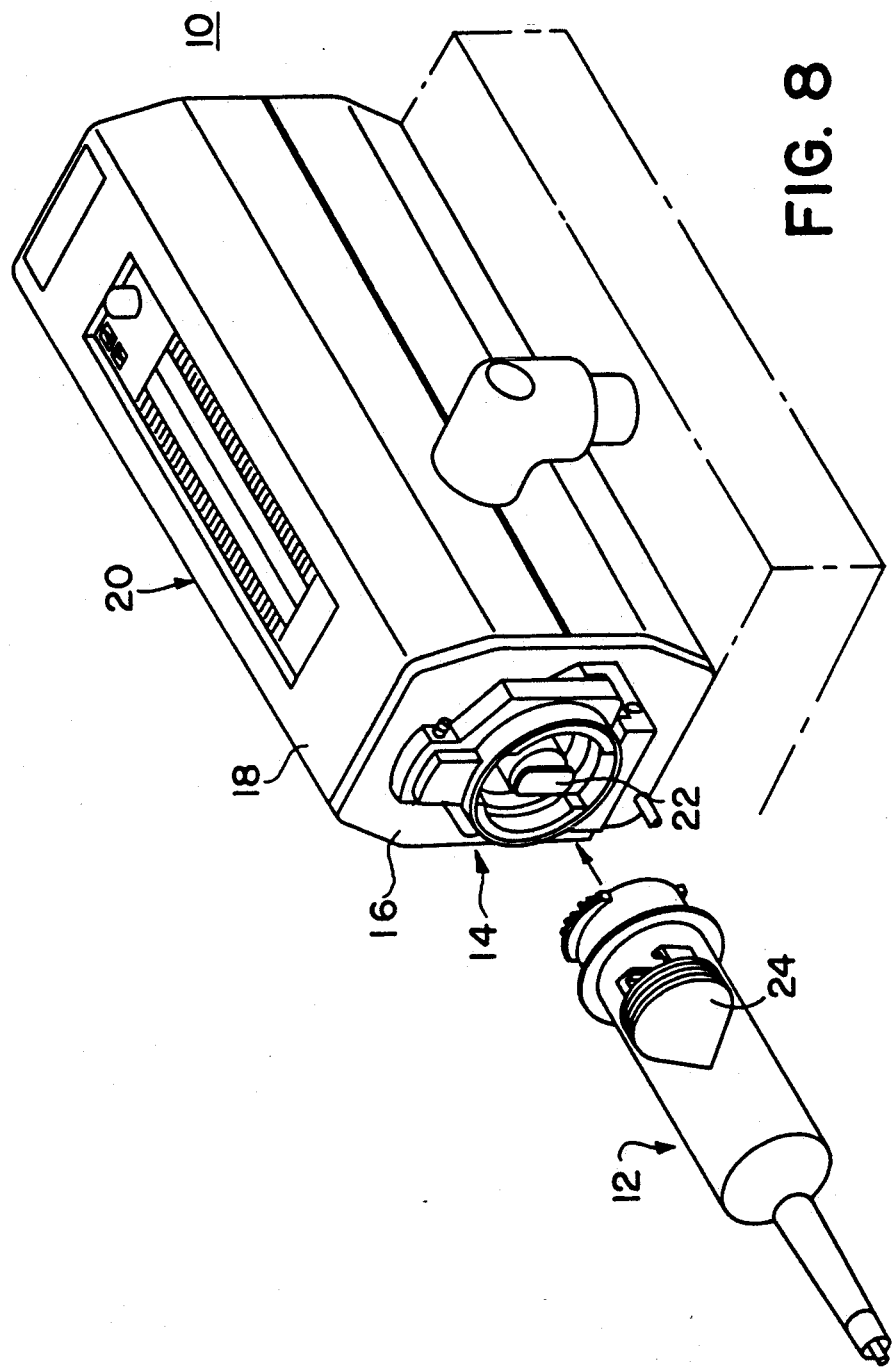

FLUID PRESENCE INDICATOR FOR ROTATABLE SYRINGE

BACKGROUND OF THE INVENTION

1. Field of the Invention

The present invention relates to means for determining the presence of a transparent liquid in a transparent angiographic syringe barrel and, more particularly, to means by which the presence of such a liquid is indicated by an alteration in the shape of an indicator pattern when viewed through the barrel.

2. Description of the Prior Art

One of the dangers involved in the injection of fluids into a patient is the risk that air will be accidentally injected into the patient resulting in an embolism. This danger is particularly acute in the case of angiographic equipment where blood vessels are studied by using x-rays while injecting a contrast medium into the body through a catheter inserted in a blood vessel. The contrast medium is frequently colorless, and because such procedures are usually performed under relatively low light levels to facilitate reading of the x-rays, the ever-present risk is magnified. It is therefore highly desirable to provide a means whereby the presence of an empty or an only partially filled syringe can be readily detected prior to the attempted injection.

One approach to the problem of fluid presence detection is set forth in U.S. Pat. No. 4,006,736, issued on Feb. 8, 1977, to Kranys et al. That patent describes two different circuits for detecting the presence of air in a syringe cartridge by monitoring motor current or utilizing a characteristic of the syringe-fluid combination. Such systems are quite complicated and expensive.

U.S. Pat. No. 330,621, issued on Nov. 17, 1885, to Reichardt, shows, in a hypodermic syringe, a glass tube in which graduation lines on the back of the tube are magnified when viewed through a liquid to facilitate reading. In the absence of the liquid, the graduations are not magnified and do not appear as though extending entirely around the transparent tube. In this way the magnification of the graduations indicates the quantity of a liquid in the syringe.

U.S. Pat. No. 1,225,604, issued on May 8, 1917, to Ernst, relates to a sight gauge which includes a spaced member having vertical rows of circular holes which appear circular when the glass tube is empty, and appear transversely elongated when water is present in the glass.

U.S. Pat. No. 4,452,251, issued Jun. 5, 1984, to Heilman, relates to a liquid indicator pattern on an angiography syringe which includes a plurality of discrete opaque patterns substantially axially disposed along the barrel of the syringe. This patent, assigned to the assignee of the subject Application, further relates to the use of an axially oriented array of fluid presence indicators applied to the barrel of a syringe or to an outer pressure jacket housing the syringe.

While the foregoing prior art disclosures relating to fluid presence detection may be useful in the particular applications described therein, they are inadequate for syringes used in connection with angiographic injectors such as those described in U.S. application Ser. No. 07/929,926, filed Aug. 17, 1992 by D. M. Reilly, et al., which is assigned to the same Assignee as the subject application. Such apparatus relates to a front-loading angiographic injector apparatus wherein a syringe of special construction is mountable upon and removable from a front wall of an injector housing. This apparatus includes a rotatable syringe which is not carried by a pressure jacket. In such an apparatus, the syringe may be rotated to engage mounting flanges to interconnect the apparatus drive member and the plunger of the syringe to inject a contrast medium into the body.

In the low-light levels typically experienced during an angiographic scan, graduations and lines such a those described in the Reichardt patent are not readily distinguishable. Similarly, the circular openings described in the Ernst patent are not useful under those conditions because they depend upon the transmission of light through the back of the syringe from all directions. In contrast, angiographic injectors are typically used with the light being directed from above. The axial display of indicator patterns described in the Heilman patent are only useful when viewed through the syringe from the side of the syringe opposite the patterns.

It is desirable therefore to provide, on the barrel of such a syringe, an array of fluid presence indicator patterns which may be visible and useable to determine the presence or absence of liquid, notwithstanding the rotational orientation of the syringe.

Accordingly, it is an object of the present invention to provide a means whereby the presence of an empty or an only partially filled syringe can be readily detected under low-light levels prior to injection by direct visual means and without the use of electronic circuitry, backlighting or the like.

It is another object of the invention to provide a means whereby the presence of an empty or an only partially filled syringed can be readily detected notwithstanding the rotational orientation of the syringe.

It is a further object of the invention to provide a fluid presence indicator array which will permit unobstructed viewing of such indicators while providing indicator locations at various points around the syringe.

It is a still further object of the invention to provide a fluid presence indicator array which will permit facile comparison of distorted and undistorted indicator patterns to readily indicate the presence or absence of liquid medium within the syringe.

SUMMARY OF THE INVENTION

Briefly stated, in accordance with one aspect of the present invention, a fluid presence indicating means is provided for use with a syringe having a transparent, hollow cylindrical barrel for receiving a transparent liquid, the barrel including a plunger axially reciprocable there within. The indicating means is positioned in the outer surface of the barrel to indicate the presence of the transparent liquid and includes a plurality of discrete patterns of predetermined shape which are disposed around the barrel. When liquid is present in the barrel, the perceived configuration of the patterns is altered and thereby provides a direct visual indication of the presence of a transparent liquid within the barrel. The patterns are arranged around the barrel in a non-overlapping, helical configuration, radially spaced approximately 120° apart in the preferred embodiment and vertically spaced so that each indicator occupies its own vertical level on the syringe.

BRIEF DESCRIPTION OF THE DRAWINGS

FIG. 1 is a side elevation of an angiographic syringe embodying the present invention filled with liquid and shown partially in section;

FIG. 2 is a sectional view of the syringe taken along line 2—2 of FIG. 1;

FIG. 3 is a view taken along line 3—3 of the syringe in FIG. 1 illustrating the appearance of an indicator as viewed through a filled syringe;

FIG. 4 is a side elevation of an empty angiographic syringe embodying the present invention and shown partially in section;

FIG. 5 is a sectional view of the empty syringe taken along line 5—5 of FIG. 4;

FIG. 6 is a view taken along line 6—6 of the syringe in FIG. 4 illustrating the appearance of an indicator as viewed through an empty syringe;

FIG. 7 is a developed view of the barrel portion of the preferred embodiment of the invention, illustrating the spatial array of the liquid presence indicators thereon.

FIG. 8 is a general perspective view of an angiographic injector apparatus showing an injector housing and a syringe, embodying the present invention, in disassembled relationship.

DESCRIPTION OF THE PREFERRED EMBODIMENT

Referring now to the drawings, in FIG. 8 thereof, there is shown an angiographic injector apparatus 10 of the type disclosed in U.S. application Ser. No. 07/929,926, filed Aug. 17, 1992 in the name of D. M. Reilly. The apparatus of FIG. 8 includes a syringe 12 capable of being front-loaded into a mounting assembly 14 on a front wall 16 of a housing 18 of an injector 20, and also capable of functioning in an injection operation without the use of a pressure jacket. In operation, syringe 12 is mounted on mounting assembly 14 by inserting and rotating syringe 12 to engage drive member 22 with syringe plunger 24.

FIGS. 1 and 4 of the drawings shows the syringe 12 with fluid presence indicators 26a-f arrayed on the barrel portion arrayed thereon. Indicators 26a-f may be of any suitable shape and dimension. In this preferred embodiment, indicators 26 are shown as vertically oriented elliptical shapes. Indicators 26 may be applied to barrel 25 of stringe 12 by any suitable means, such as etching, hot-stamping, silk-screening or the like.

In order to provide an effective indicator pattern 26, each ellipse can have a horizontal minor axis whose length is approximately 60% of the vertical major axis length. The overall dimensions of the ellipses can be chosen so that when viewed directly through a full syringe, the ellipses appear generally circular. As the dimensions of the barrel and the presence or absence of fluid in the syringe affect the resulting appearance, the dimensions can be selected so that in each combination of barrel size and content, the basically circular appearance results.

Syringe 12 in FIG. 1 is shown substantially filled with colorless liquid contrast medium 28, while in FIG. 4, syringe 12 is illustrated devoid of liquid. Liquid 28, having an index of refraction greater than that of air, acts to bend the path of visible light reflected from indicator 26c in FIG. 1 to viewer 30 as further shown in FIG. 2. The amount of deflection is a function of the curvature of the barrel 25 of syringe 12 and the index of refraction of liquid 28. Since the liquid in barrel 25 of syringe 12 assumes the cylindrical shape of barrel 25, the liquid functions as a cylindrical lens, refracting light in the dimension substantially normal to the axis of the syringe. Thus, the horizontal dimension, or minor axis, of the indicator pattern 26c appears magnified to a viewer through the filled syringe shown in FIG. 1. In an empty syringe, without the cylindrical lens formed by the liquid contrast medium, the indicator 26c does not appear magnified, but remains elliptical in appearance, as shown in FIG. 3, because the light rays are not refracted, as illustrated in FIG. 5.

Indicator patterns 26a-f are arrayed in a helical arrangement on barrel 25 of syringe 12. This arrangement of indicator patterns in the preferred embodiment is more readily illustrated in FIG. 7, which is a developed view of cylindrical barrel 25 of syringe 12. In this view, and in FIG. 2, it can be seen that the indicator patterns 26 are radially spaced 120° on center, with each succeeding indicator pattern 26 axially displaced in non-overlapping vertical relationship with its next neighboring indicator pattern.

In FIG. 7, therefore, it can be appreciated that indicator pattern 26a occupies vertical space A on barrel 25, indicator pattern 26b occupies vertical space B, indicator pattern 26c occupies vertical space C, and so on. In this fashion, at least two of indicator patterns 26 are readily visible substantially directly through barrel 25 regardless of the rotational orientation of syringe 12.

As seen in FIG. 1, therefore, indicator patterns 26c and 26f may be viewed directly by the viewer 30 to indicate the apparent circle shown at FIG. 3. The view directly illustrated in FIG. 1, however, shows that in a view substantially normal to the view afforded the viewer 30, indicator patterns 26a and 26d appear substantially magnified in horizontal dimension. The view of indicator patterns 26a and 26d is not obstructed by indicator patterns 26b and 26e, in FIG. 1, because the indicator patterns 26 are arrayed in non-overlapping vertical relationship. Besides affording an unobstructed view of the magnified indicator patterns through the liquid contrast medium, this arrangement allows simultaneous viewing of internal and external views of indicators 26a and 26b, respectively. This permits an easy comparison of the modified and unmodified shapes of indicator patterns 26a and 26b, respectively, which can be of assistance in readily determining the fluid content status of the syringe in the darkened environment in which such procedures are often carried out.

When viewed obliquely, more direct comparison of distorted and undistorted patterns is enhanced. In other words, oblique viewing of the syringe and its contents from position 30' in FIG. 2 affords a direct comparison of distorted and non-distorted patterns 26c and 26b, respectively, enabling the fluid capacity status of the syringe to be readily ascertained.

It should be readily understood that, in other embodiments, different non-overlapping arrays of indicator patterns may be used. For example, radial spacing may be varied from the 120° radial spacing shown in the preferred embodiment as long as the indicator patterns 26 are able to be viewed as substantially non-overlapping in aspect.

While the invention has been described in connection with preferred embodiments, it will be understood that it is not intended to limit the invention thereto, but it is intended to cover all modifications and alternative constructions falling within the spirit and scope of the invention as expressed in the appended claims.

What is claimed is:

1. In a rotatable angiographic syringe having a transparent, hollow, cylindrical barrel for receiving a transparent liquid, and a plunger axially reciprocal within the barrel for discharging the liquid therefrom, the improvement comprising indicator means carried by said barrel, said indicating means including a plurality of discrete patterns of predetermined shape substantially circumferentially disposed around said barrel, whereby the liquid alters the perceived configuration of said patterns when viewed through said barrel to provide a direct visual indication of the presence of a transparent liquid within said barrel notwithstanding the rotational orientation of said syringe.

2. The indicating means of claim 1 wherein said indicator means is imprinted on the outer surface of said barrel.

3. The indicating means of claim 1 wherein said patterns are substantially elliptical and have their major axis aligned with the axis of said barrel.

4. The indicating means of claim 3 wherein said elliptical patterns are of such a configuration relative to the size of said barrel that the presence of liquid there within distorts said patterns so that they appear to be circular.

5. The indicating means of claim 1 wherein said patterns are circumferentially disposed around the barrel of said syringe so that when viewed normal to the axis of said syringe, the view of each of said patterns is not substantially obscured by any other of said patterns.

6. The indicating means of claim 5 wherein said patterns are arranged in a helical array around said barrel.

7. The indicating means of claim 6 wherein said patterns are circumferentially arranged approximately 120° apart.

8. The indicating means of claim 7 wherein said patterns are disposed on said barrel whereby each of said patterns is axially displaced from each of the other of said patterns, in substantially non-overlapping vertical relationship.

9. The indicating means of claim 1 wherein said patterns are arranged so that, when viewed from a direction normal to the axis of said syringe, none of said patterns will appear to substantially obscure from view any other of said patterns.

* * * * *